United States Patent
Graumann

(10) Patent No.: US 8,886,496 B2
(45) Date of Patent: Nov. 11, 2014

(54) METHOD TO DETERMINE A PARAMETER OF A FIXING ELEMENT FOR AN IMPLANT TO BE AFFIXED TO A BONE

(75) Inventor: Rainer Graumann, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 262 days.

(21) Appl. No.: 13/302,214

(22) Filed: Nov. 22, 2011

(65) Prior Publication Data
US 2012/0130686 A1    May 24, 2012

(30) Foreign Application Priority Data

Nov. 23, 2010 (DE) .......................... 10 2010 061 777

(51) Int. Cl.
  *G06F 17/50* (2006.01)
  *A61B 19/00* (2006.01)
  *A61B 17/80* (2006.01)

(52) U.S. Cl.
  CPC .................. *A61B 19/50* (2013.01); *A61B 17/80* (2013.01); *A61B 2019/502* (2013.01)
  USPC .............................................................. 703/1

(58) Field of Classification Search
  CPC .. A61B 19/50; A61B 17/80; A61B 2019/501; A61B 2019/502; A61B 2019/504
  USPC .............................................................. 703/1
  See application file for complete search history.

(56) References Cited

U.S. PATENT DOCUMENTS

| | | | |
|---|---|---|---|
| 8,126,111 B2* | 2/2012 | Uhde et al. ..................... | 378/41 |
| 8,377,066 B2* | 2/2013 | Katrana et al. ............... | 606/86 R |
| 2004/0068187 A1* | 4/2004 | Krause et al. ................. | 600/443 |
| 2009/0275991 A1* | 11/2009 | Medoff ......................... | 606/297 |

FOREIGN PATENT DOCUMENTS

| | | |
|---|---|---|
| DE | 10 2008 051 532 A1 | 4/2010 |
| DE | 10 2008 058 305 A1 | 5/2010 |

* cited by examiner

*Primary Examiner* — Eunhee Kim
(74) *Attorney, Agent, or Firm* — Schiff Hardin LLP

(57) ABSTRACT

In a method to determine a parameter of a fixing element for an implant to be affixed to a bone, the actual design of the bone and the relative attitude of the implant positioned on this are determined, a virtual 3D model depicting the actual design of the bone and the relative attitude of the implant is generated, and a parameter of the fixing element is determined automatically using the virtual 3D model.

7 Claims, 2 Drawing Sheets

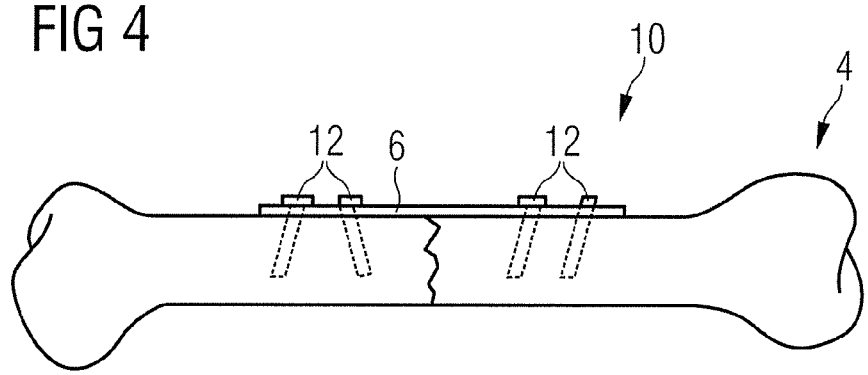
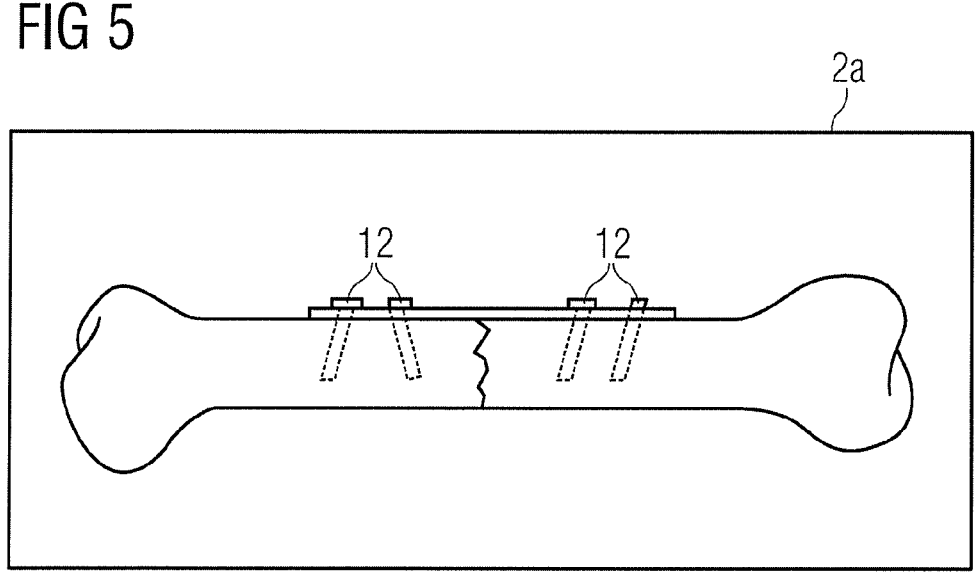

METHOD TO DETERMINE A PARAMETER OF A FIXING ELEMENT FOR AN IMPLANT TO BE AFFIXED TO A BONE

BACKGROUND OF THE INVENTION

1. Field of the Invention

The invention concerns a method to determine a parameter of a fixing element for an implant to be affixed to a bone.

2. Description of the Prior Art

Implants, for example nails and plates for fixing bones having a fracture, are used in traumatology. These implants are attached to the bone with the use of fixing elements, for example screws. For optimal attachment, these must be introduced into the body of a patient in an optimally advantageous attitude, thus in a correct position and at a correct angle. In addition to these parameters, the correct length of the fixing element also plays an important role for achieving the correct purchase (hold).

These parameters of the fixing elements have conventionally been selected corresponding to the prior clinical and anatomical knowledge of the surgeon. For example, using x-ray exposures, the surgeon decides where and how a suitable fixing element must be introduced into the body of the patient, which then occurs with x-ray monitoring. Errors can therefore occur both in the manual selection of the parameters and in the introduction of the fixing element. If the length of the fixing element is chosen too short, a sufficient purchase for the implant cannot be assured. By contrast, if the length is chosen too long, the fixing element may project from the bone and protrude into tissue surrounding the bone, or into a joint space, such that significant injuries can arise. Moreover, it is possible that the fixing elements may be inserted at an incorrect attitude (for example at a disadvantageous angle) into the bone, so an optimal stability of the implant at the bone is not ensured.

SUMMARY OF THE INVENTION

An object of the invention is to provide a method to produce a scintillator-photosensor sandwich for use in a pixel resolving radiation detector, wherein the above disadvantages are avoided.

This object is achieved by a method according to the invention that includes the following steps.

In a first step the actual configuration of the bone and the relative attitude of the implant positioned on this are accordingly determined. This can occur by the configuration, namely the shape of the bone and the bone quality, for instance the bone density, and the relative attitude of the implant positioned therein are determined by means of a radioscopy method. The bone density represents a significant factor. A bone includes the inner spongiosa with low bone density and the outer compact bone with high bone density. If possible, the fixing element should be situated in the region of the compact bone in order to achieve a high fixing strength.

In order to obtain as much of such information as possible, in particular the spatial geometry with regard to the bone and the implant positioned thereon, two optimally orthogonal images (or even multiple images) are produced, for example. The perspective from which the individual images are produced is known, so a spatial combination of the respectively obtained information is possible.

A virtual 3D model depicting the actual configuration of the bone and the relative attitude of the implant is generated in a next step. A model of the complete bone does not necessarily need to be generated. Rather, it is sufficient for the model to encompass one or more appertaining bone fragments and an adjacent joint, for example. This model then contains the information determined in the first step, for example the geometry and the bone density as well as the attitude information of the implant relative to the bone.

The parameter of the fixing element is then automatically determined in a further step using the virtual 3D model.

For example, based on the information contained in the 3D model with regard to the configuration of the bone and the corresponding relative attitude of the implant, it can initially be determined the number of fixing elements that can be used at all. The composition of the implant also plays a role as to the regions at which the implant can be affixed. Furthermore, the bone quality—thus for example its material composition and its stability—is decisive; in particular, the fixing elements must be introduced into sufficiently large bone fragments. The geometric data of the individual fixing elements (for instance their length, position and the angle at which the fixing elements are introduced into the bone) are subsequently determined such that the implant has an optimal purchase at the bone, so that the none or the individual fragments thereof are sufficiently stabilized. For example, if a defined attitude of the fixing elements has been required or established, their maximum or optimal length can be determined. At least two parameters must normally be optimally determined, namely the length and orientation of fixing elements. The position is most often already provided by the attitude of the implant (a plate, for example) and by the attitude of the regions present at the implant to which the fixing element can be attached, for instance holes present in the plate.

An intelligent method to determine optimal parameters, for example the number or the length of fixing elements, which the corresponding information delivers to the medical personnel in real time is provided by the method according to the invention. The implant can be affixed in an optimal manner based on this information, such that procedure corrections based on parameters that turn out to be incorrect are avoided. Moreover, a continuous x-ray monitoring (as has previously been required) is not necessary due to the calculation of the parameters, so the radiation exposure of the patient is minimized.

The parameter can thus be the length, position, orientation or attitude of the fixing element, or even its count, for example.

In a preferred embodiment of the method, the 3D model is generated in the second step by a virtual bone model (that, for example, exists based on statistical experimental values in a database) being adapted to the actually present bone or the bone fragment. A pre-existing model that only approximately corresponds to the actual relationships is thus adapted to the actual situation. The basis for such an adaptation can be the information obtained by means of the radioscopy method, thus for example the information that can be learned from an x-ray image.

A virtual implant model is then adapted to the now-adapted virtual bone model according to the relative position determined in the first step. For example, this implant model can be selected in a simple manner from a database since it is already known which implant is to be used. The result is then a 3D model of the bone and the implant that depicts their actual relationships.

In a preferred embodiment, after the calculation of the parameter, a model of the fixing element (which model is likewise present in a database) is virtually mixed into an image containing the bone and the implant. For example, this image then can contain the optimal attitude of a previously calculated number of fixing elements that have already been overlaid in the image at their target position. The medical personnel thus are provided with information as to how the correct, desired attitude of the fixing element is to appear in the patient and this image can be used as a template for a procedure.

Alternatively, the parameter to guide the fixing element corresponding to the virtual presentation can be used in the Surgix method, for example. Moreover, the parameter, for example, the attitude of the fixing element can be transmitted to a tool to be navigated, so the medical personnel are assisted upon introduction of the fixing element into the bone. The entire process of the introduction is thus directed by the method according to the invention, such that errors that occur given exclusive use of a template indicating only the target position are avoided.

BRIEF DESCRIPTION OF THE DRAWINGS

FIG. 4 illustrates the 3D model of FIG. 3 with fixing elements.

FIG. 5 shows the x-ray image of FIG. 2 with virtually overlaid fixing elements,

DESCRIPTION OF THE PREFERRED EMBODIMENTS

Figure 1:
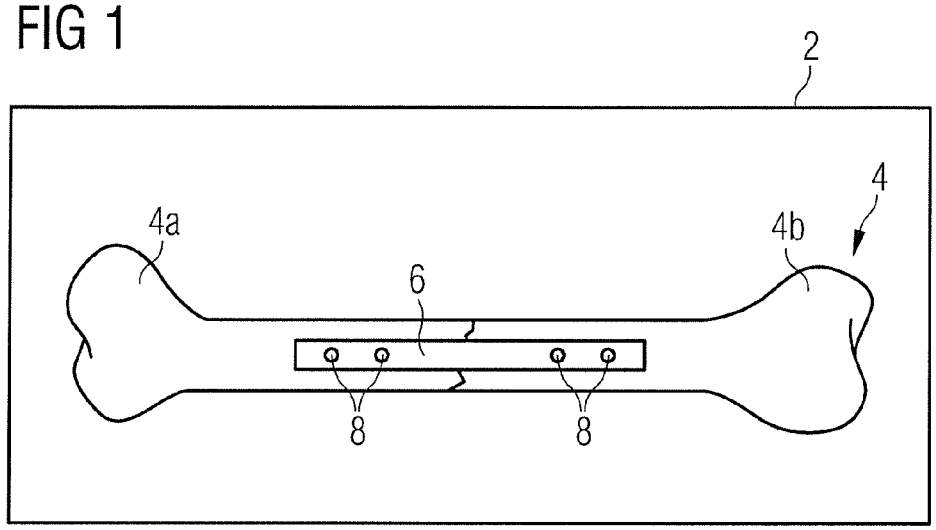
FIG. 1 shows an x-ray image displaying the actual design of a bone and the relative attitude of an implant positioned on this in a first acquisition direction.

FIG. 1 shows an x-ray image 2 produced from a first acquisition direction, in which x-ray image 2 is depicted a bone 4 that has two fragments 4a, 4b due to a fracture. To fix this bone 4 (which has already been set), an implant 6 was positioned on the bone 4 that now must itself be affixed onto the bone 4. In order to enable such a fixing, the implant 6 has a number of holes 8.

Figure 2:
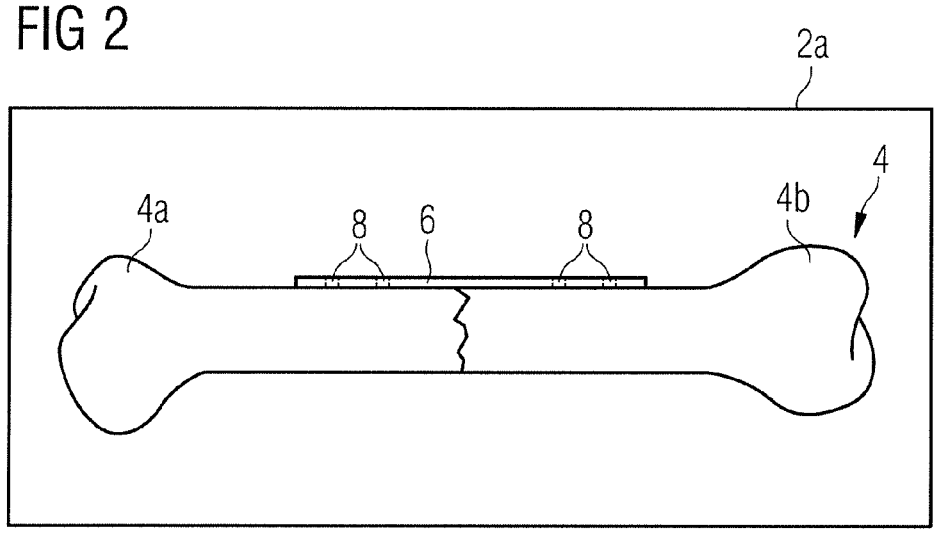
FIG. 2 shows an x-ray image displaying the actual design of a bone and the relative attitude of an implant positioned on this in a second acquisition direction.

An additional x-ray image 2a that was produced from a second acquisition direction and shows the same bones 4 as well as the implant 6 from an additional viewpoint is now shown in FIG. 2. The two x-ray images 2 and 2a were acquired respectively from orthogonal acquisition directions in order to thus achieve an optimally good data foundation with regard to the image information representing the actual spatial relationships. In order to further improve this foundation, however, it is also possible to produce a larger number of x-ray images. According to the method according to the invention, the actual configuration of the bone 4, thus the shape and the material property, for instance the configuration and the relative attitude of the implant 6 positioned on this is determined by means of the image information, for example by segmentation.

Figure 3:
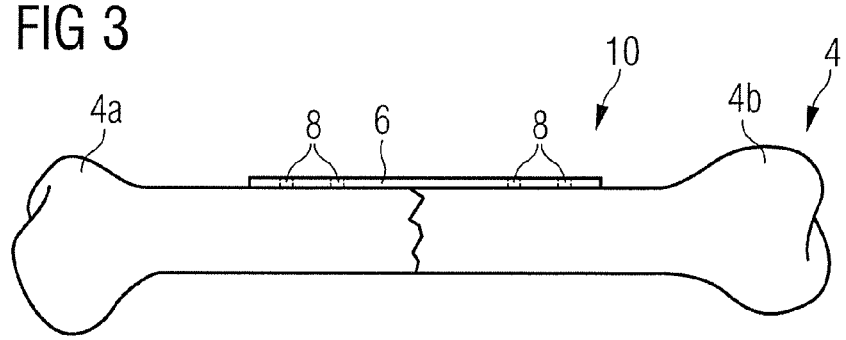
FIG. 3 illustrates a 3D model of the bone and implant shown in FIGS. 1 and 2.

In a next step a virtual 3D model 10 imaging the actual design of the bone 4 and the relative attitude of the implant 6 is now created from these acquired data, as is depicted in FIG. 3. A virtual, statistical bone model (which serves as a template and is then adapted to the actual situation with the aid of the data acquired above with regard to the actual design of the bone 4) that is contained in a database initially forms a basis for this. For example, the bone model is adapted to the actual bone diameter and to the bone length. A virtual implant model which is likewise present in a database is then adapted to this model of the bone 4 according to the relative position determined above. Then result is then an exact 3D model 10 with bone 4 and implant 6 that thus approximately represents a depiction of the actual relationships.

The parameter of a desired fixing element (of screws, for example) is now determined automatically using this virtual 3D model 10. In the shown example, the 3D model 10 is shown in FIG. 4 with multiple fixing elements 12 located in their target position, wherein the number of required fixing elements 12 as a parameter was automatically calculated at four via the method according to the invention. Furthermore, the optimal attitude—thus the position and direction of every single fixing element 12—was determined corresponding to the implant and bone geometry, such that the implant 6 has the best possible purchase on the bone; the fixing elements 12 thus have an optimally long length but do not project out of the bone 4.

In order to indicate the target position of the individual fixing elements 12 to a surgeon in the real x-ray image 2a, corresponding models of the fixing elements 12 can be overlaid in the x-ray image 2a, as is shown in FIG. 5.

Alternatively, the automatically determined attitude can also be used to guide the fixing element 12 during a surgical procedure. For this the attitude information is transmitted to a tool to be navigated, such that the medical personnel are assisted in the insertion of the fixing element 12 into the bone 4 and thus the correct target position is achieved.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to determine a parameter of a plurality of fixing elements for an implant to be affixed to a bone by said fixing elements, comprising:
   a) using medical images that represent the bone, determining an actual configuration of the bone and the implant positioned on the bone at a target position;
   b) in a computer, generating a virtual 3D model depicting the actual configuration of the bone and the implant positioned on the bone at said target position;
   c) determining parameters of the fixing elements automatically in the computer using the virtual 3D model that produce a stable attachment of said implant to said bone, said parameters comprising a number of said fixing elements and an orientation of said fixing elements; and
   d) providing a designation of said parameters of said fixing elements at an output of said computer.

2. A method according to claim 1, comprising generating said parameters to also comprise a length or attitude of the fixing elements.

3. A method according to claim 1, comprising determining said actual configuration of the bone and the implant positioned on the bone at said target position in step a) using a radioscopic image.

4. A method according to claim 1, comprising generating the 3D model in step b) by adapting a virtual bone model to said bone, and thereafter adapting a virtual implant model to the adapted virtual bone model according to said actual configuration determined in step a).

5. A method according to claim 1, comprising, in said computer, generating a model of the fixing elements that conforms to said parameters, and overlaying said model of the fixing elements on an image containing the bone and the implant.

6. A method according to claim 1 comprising supplying an electronic designation of said parameters from said computer to a navigable tool, and navigating said navigable tool relative to said bone and said implant to attach said implant to said bone at said target position with said fixing elements, according to said parameters.

7. A method according to claim 1, comprising employing a plate as said implant.

\* \* \* \* \*